(12) United States Patent
Carlsson

(10) Patent No.: US 7,285,197 B2
(45) Date of Patent: Oct. 23, 2007

(54) REGENERATION OF BIOSENSORS

(75) Inventor: Thomas Carlsson, Uppsala (SE)

(73) Assignee: Senzime Point of Care AB, Uppsala (SE)

(*) Notice: Subject to any disclaimer, the term of this patent is extended or adjusted under 35 U.S.C. 154(b) by 430 days.

(21) Appl. No.: 10/940,460

(22) Filed: Sep. 14, 2004

(65) Prior Publication Data
US 2005/0112777 A1     May 26, 2005

Related U.S. Application Data

(62) Division of application No. 09/462,394, filed on May 3, 2000, now Pat. No. 6,812,031.

(51) Int. Cl.
*G01N 27/327*     (2006.01)
(52) U.S. Cl. ............... 204/403.01; 204/402; 422/67
(58) Field of Classification Search ............... None
See application file for complete search history.

(56) References Cited

U.S. PATENT DOCUMENTS

| 4,153,513 A | 5/1979 | Edelmann et al. |
| 5,165,406 A | 11/1992 | Wong |
| 5,183,740 A | 2/1993 | Ligler et al. |
| 5,306,413 A | 4/1994 | Hayashi et al. |
| 5,411,866 A | 5/1995 | Luong et al. |
| 5,449,064 A | 9/1995 | Hogan et al. |
| 5,861,254 A | 1/1999 | Schneider et al. |

OTHER PUBLICATIONS

Kavita Thomas, "The Onset of Turbulent Flow", http://www.mas.ncl.ac.uk/-sbrooks/book/nish.mit.edu/2006/Textbook/Nodes/chap07/node5.html., Apr. 5, 1996.

*Primary Examiner*—Yelena G. Gakh
(74) *Attorney, Agent, or Firm*—Nixon & Vanderhye P.C.

(57) ABSTRACT

The invention relates to a system for continuous monitoring of analytes in a biological fluid, the system having increased life by virtue of inherent regeneration of sensors employed. An embodiment of the invention includes a biosensor, a sampling device for providing a sample of the biological fluid, device(s) for passing a flow of a background fluid through the flow passage at selectable flow rates, device(s) for injecting the sample into the flow of background fluid, and device(s) for increasing the flow rate of the combined flow. An embodiment of the invention provides device(s) for achieving a washing action at the signal generating portion.

6 Claims, 4 Drawing Sheets

REGENERATION OF BIOSENSORS

This patent application is a divisional application of U.S. patent application Ser. No. 09/462,394 filed on May 3, 2000, now U.S. Pat. No. 6,812,031.

The present invention relates in general to the field of biosensors, and in particular to methods and apparatus for regenerating such sensors, thereby increasing the effective life thereof.

In a specific aspect the invention relates to a system for continuous analysis of analytes in blood or serum comprising means for regeneration of the sensor employed therein.

BACKGROUND OF THE INVENTION

Measurements of analytes in blood is commonly performed by sampling blood from patients and analyzing said samples in a laboratory, often situated at a location remote from the ward. E.g. for glucose analysis there are available special reagent sticks usable for measuring on site i.e. in the ward. However, the accuracy of such measurements is questionable, and the error could be 10-20% at best.

Often it is necessary to perform several sequential measurements over periods of several hours, which is very labor intensive. Furthermore, the risk for errors because of the human intervention is evident, and the low accuracy is of course also a drawback in this regard.

For the purposes of this application, the term "biosensor" means any device having a portion which interacts with biological or biochemical material, and has the capability to generate a signal indicative of a change in some parameter of said biological or biochemical material as a consequence of said interaction.

When analytes such as glucose, urea, lactate, ATP, glycerol, creatinine and pyruvate in biological samples, such as blood, plasma or serum are analyzed using biosensor techniques based on immobilization of enzymes, the sensor surface will be exposed to a certain amount of sample during a certain time sufficient to achieve an adequate sensor response. It is well known that the sensor response gradually will degrade because of fouling of the surface. This in its turn is a consequence of said exposure and the interaction between the surface and the substances present in the sample that occurs. The chemical and physical composition of the sample is thereby of importance, the sample i.a. comprising red cells, blood platelets, macromolecules, electrolytes, lipids, red/ox-compounds etc. It is also known that the support material for the enzyme immobilization in biosensors based on enzyme column technology is fouled by the substances present in the sample.

In cases where selective membranes are used for protection of the sensor surface of biosensors based on enzyme electrode technology, said membranes are also fouled by such substances.

This fouling influences the sensor response by substantially reducing the life and stability of the biosensor.

DESCRIPTION OF RELATED ART

Most known metabolite sensors today are based on the amperometric principle, that is measurement of oxygen consumption or hydrogen peroxide production in electrochemical reactions. However, interference with reducing/oxidizing substances causes problems like long time drift, need for frequent calibration and short life. Regarding the sampling procedure there exist devices which, before the actual measurement, condition the blood before it enters the actual sensor by e.g. introducing a special step, such as dialysis. This is both a more complicated solution and also more expensive, since the dialysis cassette has to be replaced before a new measurement can be made.

Another known sensor principle is by utilizing the heat production when the analytes are decomposed by the appropriate enzyme for the analyte in question. This so called enzyme calorimeter principle is known from U.S. Pat. No. 4,021,307. The enzyme calorimeter disclosed therein is however not suited for direct measurement on whole blood, since the blood cells quickly will clog the column containing the immobilized enzyme, due to adsorption of blood constituents such as various cells, trombocytes, proteins etc. This effect could be circumvented to a certain extent by diluting the blood at least ten times, which will reduce the sensitivity of the measurement considerably. However such a measure would require an extra supply of a diluting solution. Another way of reducing the clogging of the column is to use a special super porous support material with a pore size larger than 10 µm. This support made from agarose, is however softer than the conventional support materials used in this field, preferably glass, and therefore are at a certain risk of (occasionally) being compressed by the blood sample, which in turn quickly will clog the column.

Thus, at present there is no reliable method and system available for the direct and continuous analysis of whole blood drawn from patients.

SUMMARY OF THE INVENTION

The present invention therefore seeks to provide an improved method of analyzing whole blood in respect of analytes such as glucose, lactate, urea, ATP, glycerol, creatinine and pyruvate wherein the drawbacks of the prior art methods are alleviated.

In particular the active life of a biosensor that is used for such analysis is prolonged by providing for reduced fouling of the sensor by regenerating the sensor in accordance with the invention.

The method according to the invention is defined in claim 1.

In a second aspect of the invention there is also provided a system for long time measurements of whole blood directly and continuously sampled from a patient, wherein the flow of the sampled blood is held at a very low rate.

The system according to the invention is defined in claim 12.

Further scope of applicability of the present invention will become apparent from the detailed description given hereinafter.

However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus not limitative of the present invention, and wherein FIG. 1 is an overview of a system according to the invention;

DETAILED DESCRIPTION OF PREFERRED EMBODIMENTS

Figure 1:
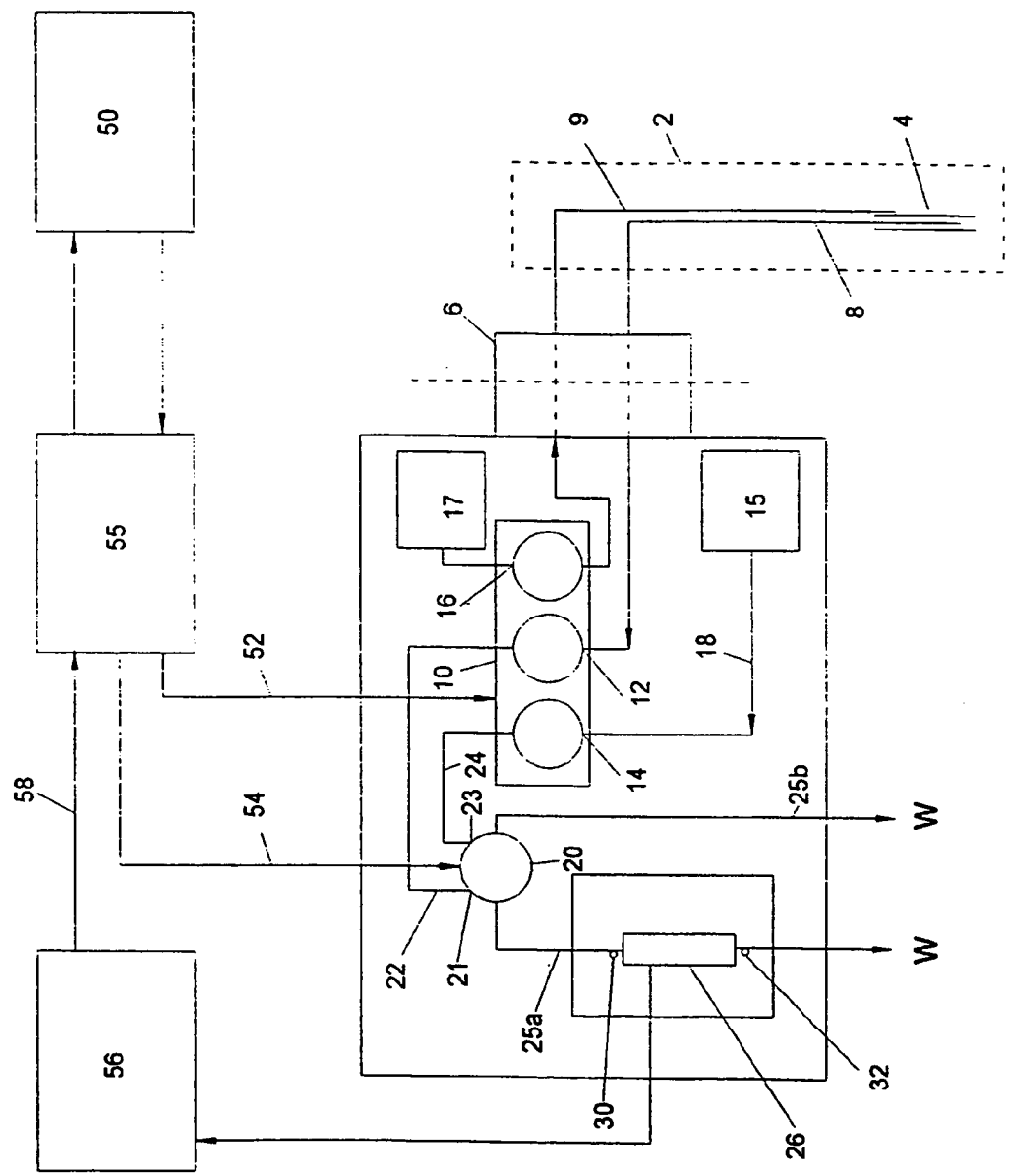

In FIG. 1 there is disclosed a system for performing a continuous monitoring of the concentration of analytes in blood.

It comprises a blood sampling device 2, such as a cannula 4 inserted in a vein of a patient. The cannula 4 is connected to the other system components via a tubing 8 and a suitable connector 6 (to be described) connecting to a pump 10, which is provided for drawing the various fluids through the system at controlled flow rates. The pump is a multichannel pump, and has a first input 12 for the blood from the sampling device 2, a second input 14 for buffer solution from a buffer storage 15, and a third input 16 for anticoagulant from an anticoagulant reservoir 17. Anticoagulant is fed through a line 9 into the sample flow in line 8 at a point near the tip of the catheter 4.

Alternatively there may be provided separate pumps for the various components.

The valve 20 is important for the operation in accordance with the invention, and has two inputs, one input 21 for sample blood, fed from pump 10 through line 22, and one input 23 for buffer, fed through line 24. There are also two outputs, a first connecting to line 25a feeding the fluid to the analysis portion, and a second connecting to line 25b for discharging the fluid as waste. The valve 20 is designed such as to permit fluid (i.e. blood in this embodiment) from line 22 to be injected into the buffer flow from line 24.

All surfaces in the system exposed to sample are coated with heparin in order to make the system blood compatible.

The actual sample analysis may be carried out in a so called enzyme reactor (ER) 26, although it is contemplated that any biosensor type may be used, provided it has a sensitive portion arranged in some kind of flow passage where flow past the sensitive portion of the sensor can be controlled. Thus, a sensor of a type that is merely immersed in a liquid would not be suitable for use with this invention. An ER is used in a preferred embodiment and will be described in more detail below.

The system also comprises a control unit 50, which may be a micro processor or a PC. An interface 55 is connected between the control unit 50 and the components in the system, such that control signals to the pump 10 and the valve 20 are fed via lines 52 and 54 respectively. Thus, the pumping rate in the various independently operated flow passages may be increased or decreased, and the valve 20 may be switched between its various positions by commands issued by the control unit in response to signals from the biosensor. An amplifier 56 is provided for amplifying the signals from the biosensor 26, and feeding said signals to the interface on line 58, for further transmission to the control unit which uses the information thus obtained to issue the appropriate control commands to the pump and valve.

The Enzyme Reactor

An enzyme reactor (ER) 26 comprises a sensor column. The column contains support material such as beads of glass or hard polymer resin, on which enzyme has been immobilized. Immobilization of enzyme is standard procedure and does not form part of this invention, and will hence not be described in detail herein.

The operation and function of the ER 26 is as follows.

The sensor column has two thermistors 30, 32, one 30 arranged at the column inlet and the other 32 at the column outlet. Fluid entering the column will begin reacting with the enzyme that is immobilized on the beads in the column, and will thereby generate heat, causing the temperature of the fluid to increase. By monitoring the temperatures at the inlet and outlet respectively, and integrating the temperature over time, the integral obtained will correspond to the heat of reaction, which then may be related to the concentration of e.g. glucose in the fluid.

Because of non-specific reactions that may be exothermic or endothermic and which occur in the column, temperature fluctuation must be accounted for. Thermostating the reactor is one way of doing this, but it can be achieved also in other ways and by other means, and is not crucial to the invention.

Operation

Returning now to FIG. 1, there is illustrated an embodiment of the system which comprises a biosensor 26 arranged in a thermostated environment. The system is operated as follows:

The catheter 4 is inserted in a blood vessel of a patient, and connected to the tubing of the system by means of a connector 6 (to be described). Initially the pump will draw blood through line 8 via line 22, through the valve 20 and to the waste line 25b for disposal, and buffer from buffer storage 15 is drawn via line 18 through the valve 20 and via line 25a into the enzyme reactor 26. The continuously measured signals obtained from the sensor when the buffer passes through it will form a background or zero level, and the flow of buffer will be referred to as a "background flow" in this application. The rate of background flow may vary in the range 0.1-10 ml/min., and preferably is 1 ml/min.

If desired, and indeed it is mostly required, anticoagulant is mixed with the blood. Normally a ratio between sample and anticoagulant of 1:1 will be used, although other ratios are conceivable for specific conditions. The anticoagulant is pumped in line 9 and injected in the sample flow line 8 near the catheter 4 tip.

At a time when it is desired to make a measurement the valve is given a "SWITCH TO INJECTION MODE" command to the effect that the blood is redirected into the buffer stream, for a period of time of a duration sufficient for an aliquot of 10 µl to be entered as a liquid plug in the buffer stream (other sample volumes may of course be employed, but at the present time 10 µl has proven suitable in most cases). This "blood plug" is passed in line 25a, which runs in the thermostated medium, where the sample obtains a controlled temperature, and then it enters the ER 26.

As soon as the blood, containing e.g. glucose, reaches the ER 26, the glucose will start reacting with the enzyme, thereby evolving heat of reaction. The enzyme reaction is a very rapid process. Other components in the blood, such as various cells, trombocytes and proteins having a tendency to adsorb to the material inside the reactor, will begin to adsorb. The latter process is however a slow process compared to the diffusion controlled enzyme reaction. The small glucose molecules diffuse very much faster than the macromolecules and other macro components in the blood.

The thermistor 32 at the output end of the ER 26 will experience a rise in temperature caused by the enzyme reaction occurring in the reactor (at this time the entire sample preferably should have entered the reactor, although this is not absolutely necessary, as will be discussed below).

In the present embodiment the temperature increase sensed by thermistor 32 is transmitted to the control unit which is programmed to respond to an increase in the temperature signal to issue a INCREASE BUFFER FLOW RATE command to the pump 10 to increase the rate of flow of the buffer by 5-100%, preferably by 10-50%, most preferably by 15-30%.

By balancing the flow rates, i.e. defining a suitable ratio between background flow rate and increased flow rate, it is possible to create a situation where larger components, such as cells, proteins etc, are washed away before they have had an opportunity to adsorb on the active surfaces inside the ER 26, and at the same time allow the smaller molecules of interest sufficient time to react with the enzyme to such an extent that it is possible to detect the reaction.

This balancing of flow ratios within the given limits is made by straight forward routine experimentation for a given system, and is easily done by the skilled man.

In an alternative embodiment it may be sufficient if only a fraction of the sample has entered the reactor. In this case the detection of signal onset is not used for triggering. Instead a certain time is determined empirically, namely the time it takes for the sample to just about reach the reactor after injection into the background flow. This time is then programmed into the control unit and used as a starting point for increaseded flow. This time can of course be selected such that different fractions of sample enter the reactor. It should be noted that if only a very minor fraction has entered when increaseded flow is initiated, the signal will be low; however, in most cases the entire sample will have reached the reactor by virtue of the void volume of the reactor being substantially larger than the sample volume.

It could also be possible to wait a short time, such as up to 5 seconds, after the sample completely has entered the reactor, i.e. after the detection by thermistor 32, before increasing the flow. Thus, in fact there is a time interval during which increased flow can be performed. The actual set of parameters has to be found empirically for each individual system, and the skilled man will be able to find these parameters without inventive work.

The flow pulse at the higher flow rate is maintained until a preselected signal value from the reaction response has been recorded, e.g. a peak maximum, and at this point the flow will be decreased by a RETURN TO NORMAL FLOW command to the pump 10, thereby stopping the additional flow of buffer solution. The duration of the pulse of increased flow rate may be 10-60 s, preferably 20-40 s.

Temperature fluctuations may be eliminated by thermostating the system, e.g. having the ER 26 immersed in a controlled temperature bath.

Figure 4:
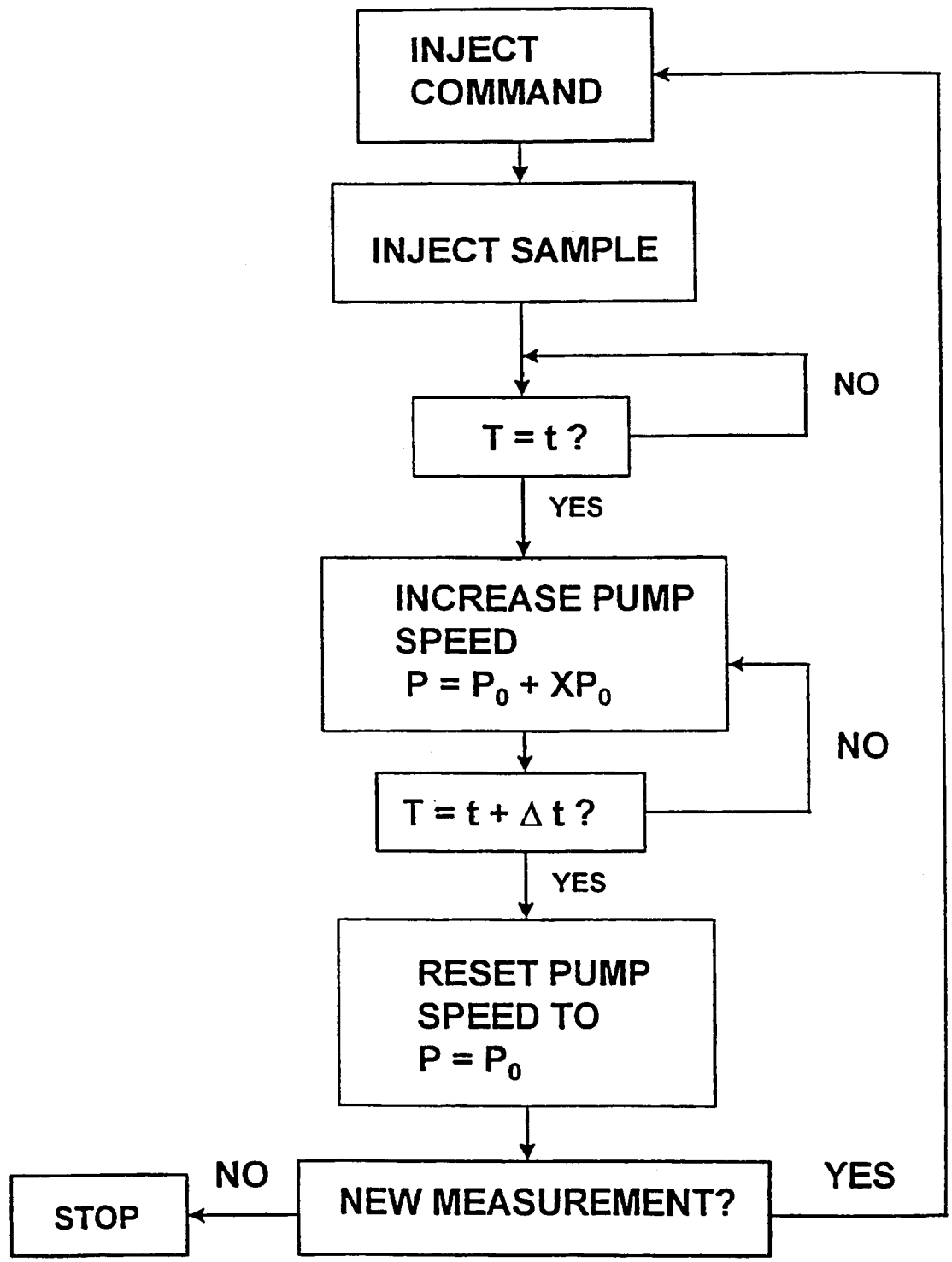
FIG. 4 is a flow chart illustrating the sequence of steps in the method of the invention.

FIG. 4 illustrates the control algorithm in a simplified flow chart form.

When it is desired to make a measurement, the operator may select a INJECT command from a menu, or the computer may be programmed to issue the command at a preselected point in time. This command will set the valve such that the flow of sample (blood) is diverted into the buffer flow, for a time sufficient to inject the desired sample volume, i.e. 10 µl. Then, the valve is reset to normal mode, i.e. the blood is discharged as waste.

If the system parameters, such as configurations, flows etc. are well defined, then it is possible to preset the time T when increased flow is to be initiated. Thus, when the elapsed time t after injection of sample equals T, increasing is initiated by the computer.

Alternatively, the computer continuously registers the signal from the thermistor, and when a signal gradient, i.e. a temperature rise, of sufficient magnitude occurs, increasing the flow is initiated.

The increase in flow is performed by increasing the pump speed, by the computer issuing a INCREASE PUMP SPEED command to the interface, such the initial pump rate $P_0$ is increased by a factor corresponding to an increase of 5-100%, preferably by 10-50%, most preferably by 15-30%. Thus, the pump speed during increased flow (or pulse) mode is $$P=P_0+XP_0.$$

After a time $\Delta t$ when the reaction in the reactor is complete, the pump speed is reverted back to the initial value $P_0$.

Then, control reverts to the computer for either a programmed new measurement at a preselected point in time, or an operator initiated measurement.

The Connector

Figure 2:
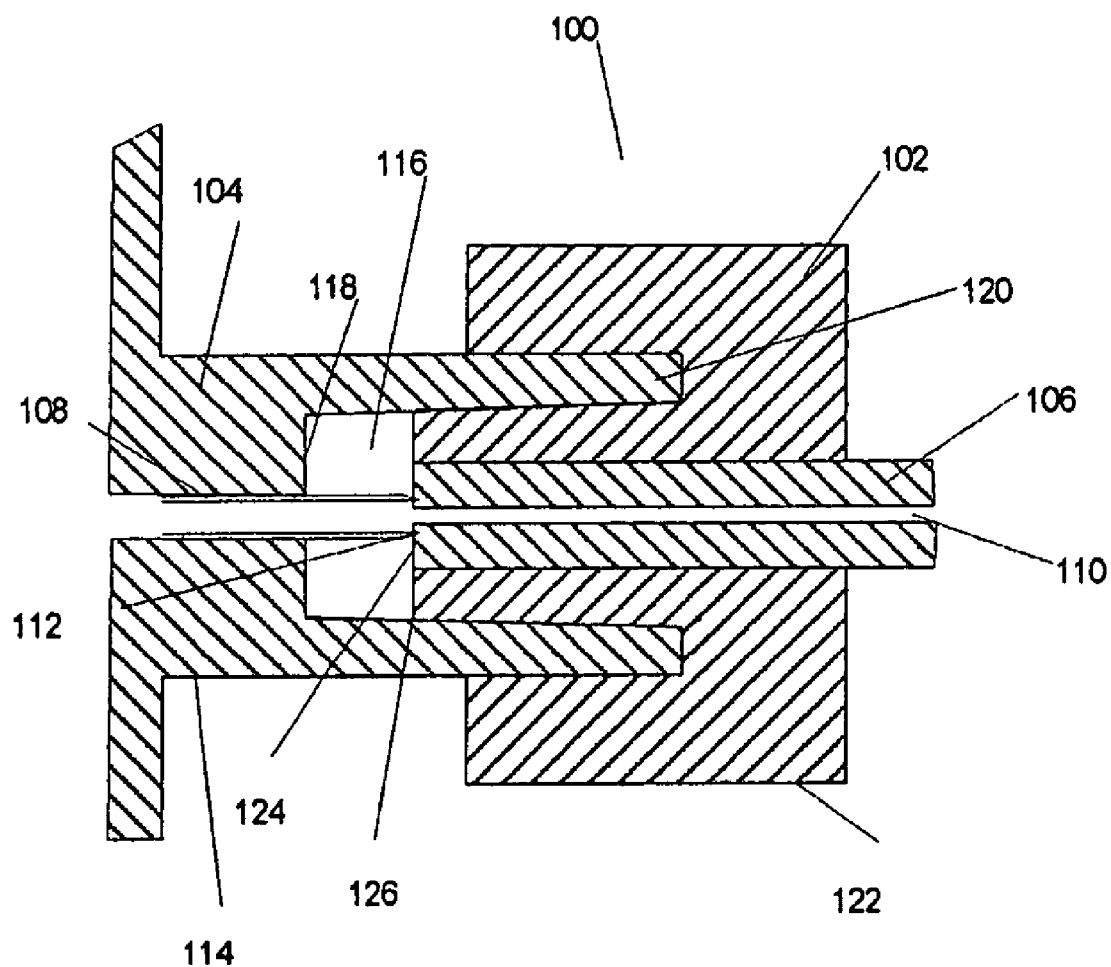
FIG. 2 is a cross sectional view through a connector according to the invention.

In FIG. 2 a connector device for connecting to a patient, suitable for use in connection with the system according to the invention is illustrated.

The connector device, generally designated 100, comprises a male part, generally designated 102, and a female part, generally designated 104.

The male part 102 is provided on the distal end of a catheter 106 that has been inserted in e.g. a blood vessel of a patient.

The female part 104 comprises a narrow tube 108 of e.g. steel, the inner diameter of which is larger than the inner diameter of the lumen 110 of the catheter 106. The ratio between diameters is preferably 2-3:1. Furthermore, the steel tube 108 is milled or ground on its outer proximal end such that a sharp cutting edge 112 is formed, i.e. the outer surface is made slightly conical at the proximal end.

The tube 108 is inserted in and fixed centrally of a concentric socket structure 114, forming said female part 104. The socket 114 thus comprises a cylinder like element having a circular/cylindrical opening or bore 116, the inner surface of which is slightly tapered, and in the center of which the tube 108 protrudes a fractional distance of the depth of said opening. Thus the cutting edge 112 of the tube 108 is located somewhere in the region between the bottom 118 of said opening 116 and its peripheral edge 120. The tapering is such that the diameter at the bottom 118 is slightly smaller than the diameter at the peripheral edge 120.

Similarly, the catheter is located centrally of a cylindrical member 122 forming the male part 102, the outer diameter of which snugly fits inside the opening of the female part 104. The end surface 124 of the catheter 106 is flush with the end surface 126 of the cylindrical member 122. The tube 108 extends so much away from the bottom 118 of the female part that when the male and female parts are connected, the sharp edge 112 will penetrate the end surface of the catheter 106.

The catheter 106 is made of a material that is enough resilient or soft, that when the male and female parts are connected, the cutting edge 112 sinks into the end surface 124 of the catheter 106. Thereby a reliable and safe connection is provided in the transport of blood from the patient to the measuring system. Suitable materials for the catheter are e.g. soft PVC/silicone.

An example of a suitable locking device usable with the connector and having a male/female structure as outlined above is a Luer®-type lock.

As can be seen in the figure there is an abrupt change in the flow cross-section at the connection between catheter 106 and tube 108. This is essential in the sense that it will prevent or alleviate clogging of the flow path. This principle is known.

Figure 3:
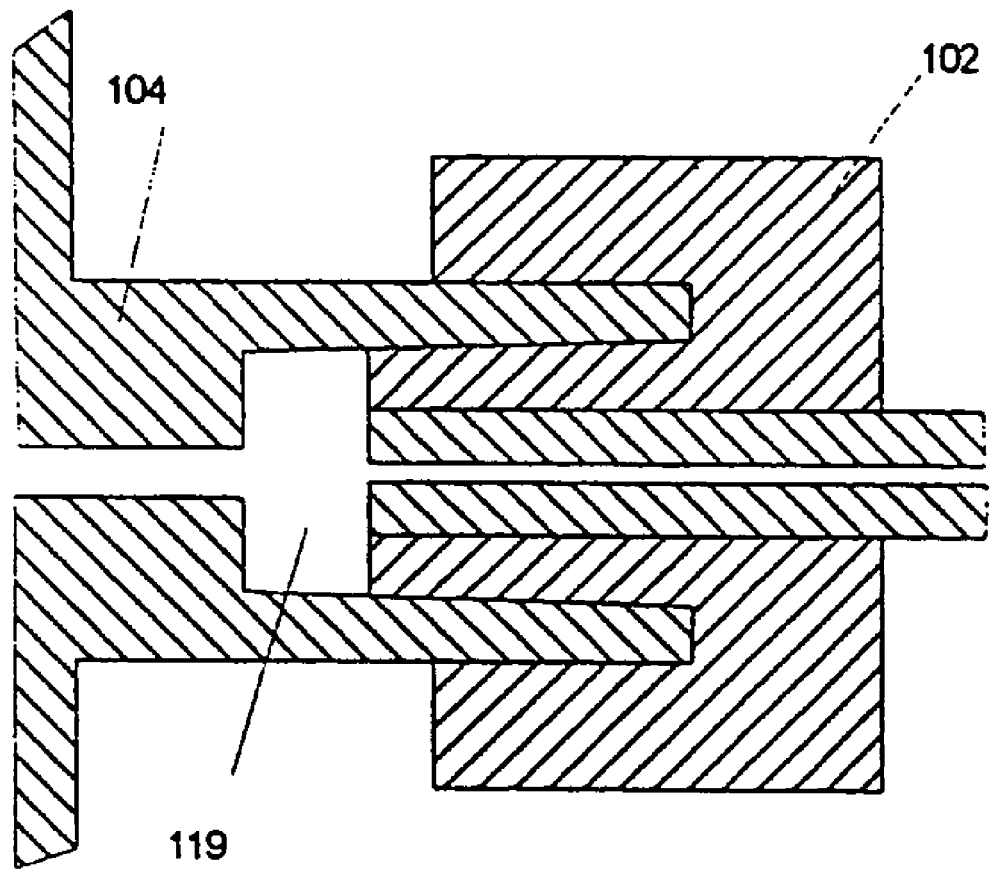
FIG. 3 is a view similar to FIG. 2, but showing a conventional connector without the inventive sealing feature.

By providing the direct contact connection between tube 108 and catheter 106, as disclosed above, the large volume 116 is eliminated from the flow path. This is important in the sense that if the blood would have to pass such a large volume before entering the tube 108, there would be enough time for the constituents of the blood to adhere to the inner surfaces of said volume 116. In FIG. 3 a connector comprising an ordinary Luer-lock type coupling is shown. The male part 102 and the female part 104 are connected such as to form a dead space 119. It is self evident that the flow rate will decrease drastically when the blood enters the large dead space 119 inside the coupling, thereby giving the blood constituents time to adhere to the inner surface of the connector and eventually clog the connector.

Of course it is equally conceivable to provide the catheter in the female part and the tube in the male part. However, the first embodiment is preferred since the sharp edge of the tube will be protected if arranged "inside" the female part, as shown.

Other types of couplings are of course conceivable, the important feature is the provision of a sharp edge on the tube, and a catheter having the necessary softness or resiliency that the edge will actually sink into the material when the parts are connected.

For example one could envisage some type of screw and nut connector, or a bayonet type coupling.

The invention will now be further illustrated by way of the following non-limiting Examples.

EXAMPLES

The following Examples were performed with the setup shown in FIG. 1. The sensor was an enzyme reactor having dimensions 20 mm length×4 mm diameter.

The skilled man will easily be able to select suitable thermistors having the appropriate properties. One example of thermistor is obtained from Victory Eng. Inc.

The sample volume was 5 or 10 µl, and the background flow was 1 ml/min.

Signal values are given in Volts.

Example I (comparative)

In this example the flow was kept constant, and thus no increased flow was applied. The sample (blood) volume was 5 µl, and the base line signal was recorded before and after detection was made. Three consecutive runs were performed.

Signal/V

| Sample No. | Before det. | After det. |
| --- | --- | --- |
| 1 | 0.10 | 0.15 |
| 2 | 0.15 | 0.23 |
| 3 | 0.22 | 0.34 |

As is clearly demonstrated the baseline signal before detection increases from 0.10 to 0.22 V, and also the baseline signal after detection increases from 0.15 to 0.34 V.

Example II (comparative)

The experiment of Example I was repeated with a fresh sensor and new samples.

| Sample No. | Before det. | After det. |
| --- | --- | --- |
| 4 | 0.14 | 0.38 |
| 5 | 0.35 | 0.63 |

Again the base line signals clearly are not reproducible between runs.

Example III (comparative)

In this example the flow was also kept constant but a sample prepared from a standard solution and glucose was introduced, and passed through the reactor.

| Sample No. | Before det. | After det. |
| --- | --- | --- |
| 6 | 0.30 | 0.31 |
| 7 | 0.29 | 0.31 |

As can be seen, the base line signal is not affected.

Example IV (comparative)

The same conditions as in Example I, but the sample volume is increased to 10 µl.

| Sample No. | Before det. | After det. |
| --- | --- | --- |
| 8 | 0.55 | 0.64 |
| 9 | 0.59 | 0.67 |
| 10 | 0.62 | 0.70 |

Again, the base line is not reproducible between runs.

Example V (According to the Invention)

In this example the sample volume was 10 µl. When the onset of sensor response was detected, the buffer flow was increased by 15% and maintained at that level for 20 seconds, when the response signal began to decrease again.

| Sample No. | Before det. | After det. |
| --- | --- | --- |
| 11 | 0.23 | 0.22 |
| 12 | 0.23 | 0.22 |
| 13 | 0.23 | 0.22 |
| 14 | 0.22 | 0.22 |
| 15 | 0.21 | 0.22 |
| 16 | 0.20 | 0.22 |
| 17 | 0.21 | 0.22 |
| 18 | 0.21 | 0.21 |
| 19 | 0.23 | 0.21 |

As can be seen from the table, 9 consecutive runs were made and the base line returned reproducibly to the same level within the accuracy that measurements allow.

The system described herein is preferably designed as a "bed-side monitor", i.e. a portable system for making around-the-clock surveillance of e.g. intensive care patients, or patients undergoing dialysis.

The control unit and other hardware components are thereby integrated in one single piece of equipment that is easily moved from one location to another.

Although the description has been made with reference to a system and method for analyzing analytes in blood, it is equally possible to use the inventive ideas for other types of complex biological/biochemical media, such as fermentation media, animal cell culture media.

For example it is suitable for analyzing ethanol or residual sugar in mash in brewing processes. It could also be used for analyzing various substances, e.g. insulin, amino acids or growth hormone in cell culture media.

It could also be used to analyze various components in milk or similar foodstuffs.

The skilled man could envisage numerous other applications of the basic principle of the invention, and implement them without inventive work.

Such variations are not to be regarded as a departure from the spirit and scope of the invention, and all such modifications as would be obvious to one skilled in the art are intended to be included within the scope of the following claims.

The invention claimed is:

1. A system for continuous monitoring of analytes in a biological fluid, the system having increased life by virtue of inherent regeneration of sensors employed, the system comprising:
   a) a biosensor of the type having a flow passage through which fluid is being passed at selectable flow rates, and a sensitive element located in said flow passage which is responsive to some component or property of a biological fluid;
   b) means for providing a signal from said sensitive element;
   c) a sampling device for providing a sample of said biological fluid;
   d) means for passing a background flow through said flow passage at controlled flow rates;
   e) means for injecting said sample into said background flow at selectable points in time;
   f) means for increasing the flow rate of said background flow during passage of the sample through said flow passage in order to achieve a washing action on the signal generating portion, wherein the means comprises a control unit programmed to respond to signals from said biosensor.

2. The system of claim 1, wherein said sampling device comprises a catheter insertable in a blood vessel of a human or an animal, and tubing connecting the catheter to the system.

3. The system of claim 1, wherein said means for passing a background flow through said flow passage at controlled flow rates comprises a pump and appropriate tubing.

4. The system of claim 1, wherein said means for injecting said sample into said background flow comprises a valve switchable between injection and waste disposal modes.

5. The system of claim 1, wherein said means for providing a signal from said signal generating portion comprises at least one thermistor.

6. The system of claim 1, further comprising a connector, for connecting said sampling device to said means for passing a background flow through a control passage at controlled flow rates, the connector comprising:
   a male and a female part;
   a tube of a hard material such as steel having an inner diameter, and being inserted in the center of one of said male and female parts and protruding from an end surface of said part;
   a catheter of a soft material inserted in the center of the other of said male and female parts and having an inner diameter substantially smaller than the inner diameter of said tube, and having an essentially flat end surface, wherein
   the protruding end of said tube is ground such as to form a sharp circumferential edge, and wherein
   the positions of said tube and said catheter in their respective male or female part are such that when said male and female parts are connected, said sharp edge penetrates into said catheter, thereby forming a fluid tight connection.

* * * * *